United States Patent
Pichot et al.

(10) Patent No.: US 9,730,880 B2
(45) Date of Patent: Aug. 15, 2017

(54) COSMETIC OR DERMATOLOGICAL COMPOSITION COMPRISING ALKYL POLYPENTOSIDE VESICLES, AND METHOD FOR PREPARING THE SAME

(71) Applicant: LVMH RECHERCHE, Saint Jean de Braye (FR)

(72) Inventors: Angelique Pichot, Saint Jean de Braye (FR); Valerie Alard, Orleans (FR); Thierry Pouget, Saint Cyr en Val (FR); Dominique Scattarelli, Orleans (FR); Cedric Ernenwein, Nouvion le Vineux (FR); Boris Estrine, Nanteuil la Foret (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 14/352,593

(22) PCT Filed: Oct. 19, 2012

(86) PCT No.: PCT/FR2012/052403
§ 371 (c)(1),
(2) Date: Apr. 17, 2014

(87) PCT Pub. No.: WO2013/057455
PCT Pub. Date: Apr. 25, 2013

(65) Prior Publication Data
US 2014/0343081 A1 Nov. 20, 2014

(30) Foreign Application Priority Data
Oct. 20, 2011 (FR) ...................................... 11 59507

(51) Int. Cl.
| | |
|---|---|
| *A61K 8/60* | (2006.01) |
| *A61K 8/34* | (2006.01) |
| *A61K 8/14* | (2006.01) |
| *A61K 8/49* | (2006.01) |
| *A61Q 19/00* | (2006.01) |

(52) U.S. Cl.
CPC ............... *A61K 8/604* (2013.01); *A61K 8/14* (2013.01); *A61K 8/34* (2013.01); *A61K 8/4973* (2013.01); *A61K 8/602* (2013.01); *A61Q 19/00* (2013.01)

(58) Field of Classification Search
CPC ............... A61K 8/60; A61K 8/34; A61K 8/14
See application file for complete search history.

(56) References Cited

U.S. PATENT DOCUMENTS

| | | | | |
|---|---|---|---|---|
| 5,605,651 | A * | 2/1997 | Balzer | ........................... 424/401 |
| 5,853,711 | A * | 12/1998 | Nakamura | ............... A61K 8/02 |
| | | | | 424/401 |
| 6,251,425 | B1 | 6/2001 | Mathur | |
| 6,596,779 | B1 * | 7/2003 | Jean-Noel et al. | ............. 516/72 |
| 2002/0197228 | A1 * | 12/2002 | LaSala | ................... A45D 34/04 |
| | | | | 424/70.12 |
| 2005/0136081 | A1 * | 6/2005 | Kawa et al. | .................. 424/401 |
| 2012/0027824 | A1 | 2/2012 | Ernenwein et al. | |

FOREIGN PATENT DOCUMENTS

| | | |
|---|---|---|
| DE | 19634374 | 3/1998 |
| EP | 1750834 | 2/2007 |
| FR | 2945208 | 11/2010 |
| FR | 2959140 | 10/2011 |
| WO | WO 00/19980 | 4/2000 |
| WO | WO 2005/110588 | 11/2005 |
| WO | WO 2008/135646 | 11/2008 |

OTHER PUBLICATIONS

Kiwada et al.: "Application of Synthetic Alkyl Glycoside Vesicles as Drug Carriers. I. Preparation and Physical Properties"; Chemical & Pharmaceutical Bulletin, Pharmaceutical Society of Japan, vol. 33, No. 2, Feb. 1, 1985, pp. 753-759, XP002129540.

* cited by examiner

*Primary Examiner* — Shirley V Gembeh
(74) *Attorney, Agent, or Firm* — Hamre, Schumann, Mueller & Larson P.C.

(57) ABSTRACT

The present invention relates to a cosmetic or dermatological composition containing a continuous aqueous phase in which are dispersed vesicles based on at least one alkyl polypentoside, and also comprising at least one alcohol and at least one surfactant.
More precisely, the cosmetic or dermatological composition comprises at least one cosmetic or dermatological active agent and at least one continuous aqueous phase in which are dispersed vesicles,
said vesicles comprising at least one alkyl polypentoside obtained by reaction of a pentose and of at least a first and a second fatty alcohol comprising a different number of carbon atoms ranging from 10 to 12, said polypentoside having an average polymerization degree of less than or equal to 2, and
said composition also comprising at least one surfactant having a HLB of less than 10, and at least one alcohol containing from 1 to 5 carbon atoms.
The present invention also relates to a process for preparing the composition, which consists in placing a mixture comprising alkyl polypentoside, the surfactant and the alcohol in contact with an aqueous phase with stirring.

21 Claims, 1 Drawing Sheet

COSMETIC OR DERMATOLOGICAL COMPOSITION COMPRISING ALKYL POLYPENTOSIDE VESICLES, AND METHOD FOR PREPARING THE SAME

The present invention relates to a cosmetic or dermatological composition comprising an alcohol, a surfactant and an alkyl polypentoside. The invention also relates to a process for preparing such a composition.

Alkyl polyglycosides are amphiphilic molecules formed from a hydrophilic part consisting of a saccharide grafted onto a lipophilic part consisting of an alkyl radical. These compounds can form vesicles in aqueous phase and under certain conditions.

Document DE 19634374-A1 describes vesicle dispersions formed with alkyl polyglycosides (abbreviated as APG) of formula (1):

$$RO(G)_n \quad (1)$$

in which R is a linear aliphatic radical containing from 12 to 22 carbon atoms, G represents a saccharide or an oligoside, and the degree of polymerization n of the sugar is between 1 and 2. These vesicles are prepared from a mixture of the saccharide or of the oligoside (product A) with a linear fatty alcohol of 12 to 22 carbon atoms (product B) in an A/B mass ratio ranging from 10/1 to 1/2. The saccharide is preferably glucose.

French patent application FR 10/01755 filed on Apr. 23, 2010 and not as yet published discloses alkyl polypentosides of formula (2):

$$RO(X)_n \quad (2)$$

in which R is a linear or branched aliphatic alkyl radical, with or without unsaturation, X is a xylose and n is between 1 and 1.5. According to the teaching of that document, these alkyl polyglycosides have the advantage of being able to form vesicles in compositions whose continuous phase consists of water, but also in compositions whose continuous phase is a fatty phase.

However, the Applicant has been able to observe that certain alkyl polypentosides have the drawback of crystallizing over time when they are dispersed in cosmetic or dermatological compositions with an aqueous continuous phase.

The Applicant has also found that the formulation of vesicles formed from certain alkyl polypentosides is unstable over time during their incorporation into a cosmetic composition by formulation in a mixture of oil, water and gelling agent, but also by simple dilution in water. Now, maintaining the integrity of the structure of vesicles is essential both for conserving the texture and the organoleptic properties of the composition, and for conversing any active agents that the vesicles convey.

The formulation of compositions with an aqueous continuous phase should thus be optimized to prevent the crystallization of alkyl polypentosides and to maintain the integrity of the vesicles, while at the same time conserving the conditions that allow the alkyl polypentosides to form vesicles in the aqueous phase.

The inventors have demonstrated that in aqueous medium, it is essential to select the nature of the alkyl polypentosides that are capable of forming vesicles and to add thereto compounds so as to prevent any instability over time, reflected, for example, by the crystallization of polypentosides.

This result has been obtained by means of the composition of the invention, which comprises, besides a particular alkyl polypentoside, at least one particular surfactant and at least one particular solvent.

It has been demonstrated that in order to obtain a stable composition whose continuous phase is aqueous and which comprises vesicles based on alkyl polypentosides, it is necessary to add to the aqueous continuous phase at least one surfactant having a HLB of less than 10, and also an alcohol comprising from 1 to 5 carbon atoms.

The inventors have also demonstrated that the compositions of the invention, once applied to the skin, can significantly improve the cutaneous penetration of active agents encapsulated in the vesicles.

One subject of the present invention is thus a cosmetic or dermatological composition comprising at least one cosmetic or dermatological active agent and at least one continuous aqueous phase in which are dispersed vesicles,
  said vesicles comprising at least one alkyl polypentoside obtained by reaction of a pentose and of at least a first and a second fatty alcohol comprising, independently of each other, a number of carbon atoms ranging from 8 to 12, each of these fatty alcohols possibly being saturated or unsaturated, and linear or branched, said polypentoside having an average polymerization degree of less than or equal to 2, and
  said composition also comprising at least one surfactant having a HLB of less than 10, and at least one alcohol containing from 1 to 5 carbon atoms.

Amphiphilic molecules—in particular alkyl polyglycosides—which are formed from a hydrophilic head linked to a lipophilic group—organize into a bilayer (or double layer) in the presence of water.

The term "vesicles" means essentially spherical supramolecular aggregates, of micron or submicron size (generally from 0.1 to 10 µm), consisting of several layers of amphiphilic molecules. They are also occasionally referred to as "liposomes" by structure analogy, although the amphiphilic molecules which constitute the vesicles of the invention are not lipids.

The vesicles may be multilamellar (abbreviated as MLV) when they consist of a stack of several double layers of amphiphilic molecules, or unilamellar (abbreviated as ULV) when they consist of a single double layer. Multilamellar vesicles comprise inside their structure several aqueous compartments, located between the bilayers and the core, whereas unilamellar vesicles contain only one at their center.

The vesicles of the invention are advantageously multilamellar. This may be observed by electron microscopy after cryofracture.

The term "stable" vesicle means a vesicle whose mean size during storage at a temperature of between 4° C. and 50° C., for a duration of at least 30 days and preferably for at least 90 days at 4° C., is constant.

The term "dilutable" refers to the possibility of diluting the vesicles in water to a dilution factor ranging from 1 to 30 times and preferably ranging from 2 to 100 times, without substantially modifying the shape or size of the vesicles.

The pentose may be chosen from xylose, arabinose, ribose and xylulose, in alpha or beta isomer form, of the L or D series, and in its furanose or pyranose form.

According to one embodiment, the pentose is xylose, in alpha or beta isomer form, of the L or D series. D-Xylose is preferred.

The average polymerization degree of the pentose is less than or equal to 2, preferably between 1 and 1.8, more preferably between 1.3 and 1.6 and more preferentially ranging from 1.4 to 1.6, and advantageously equal to about 1.5.

The alkyl polypentoside is obtained by reacting a pentose and at least a first and a second fatty alcohol comprising, independently of each other, a number of carbon atoms ranging from 8 to 12 and preferably ranging from 8 to 10. The term "fatty alcohol" means an alcohol comprising from 8 to 12 carbon atoms, said alcohol being aliphatic (i.e. not aromatic, not comprising any conjugated carbon-carbon double bonds affording aromaticity) and comprising an —OH function.

The first and the second fatty alcohol are different. They preferably have a different number of carbon atoms. The fatty alcohols are preferably both linear and saturated.

The first fatty alcohol is saturated or unsaturated, linear or branched, and comprises a number of carbon atoms ranging from 10 to 12. The first fatty alcohol is preferably linear, saturated and comprises, for example, 10, 11 or 12 carbon atoms, and preferably 10 carbon atoms. 1-Decanol is preferred.

The second fatty alcohol is preferably saturated or unsaturated, linear or branched, and comprises a number of carbon atoms ranging from 8 to 9. It is preferably linear and saturated and comprises 8 carbon atoms. 1-Octanol is preferred.

According to one embodiment, the first fatty alcohol is linear, saturated and comprises 10 to 12 carbon atoms, and/or the second fatty alcohol is linear, saturated and comprises 8 or 9 carbon atoms. Preferably, the first fatty alcohol is 1-decanol-1 and/or the second fatty alcohol is 1-octanol.

The mass ratio between the first and the second fatty alcohol is advantageously between 80/20 and 99/1, preferably between 85/15 and 95/5 and especially about 90/10.

A preferred alkyl polypentoside is obtained from D-xylose, 1-decanol and 1-octanol, and the ratio between the 1-decanol and the 1-octanol is between 80/20 and 99/1, preferably between 85/15 and 95/5 and more preferably equal to about 90/10.

The composition of the invention advantageously comprises from 0.01% to 20% by total weight of alkyl polypentoside, preferably from 0.1% to 10% by weight of alkyl polypentoside and more preferably from 0.1% to 5% by weight of alkyl polypentoside.

The alcohol advantageously comprises from 1 to 5 carbon atoms. It is preferably aliphatic (i.e. cyclic or acyclic, saturated or unsaturated, and nonaromatic), and chosen from monoalcohols and diols.

The monoalcohol is preferably chosen from ethanol, 1-butanol and 1-pentanol. The diol may be 2,3-butylene glycol or 1,2-propanediol (also known as propylene glycol).

The composition advantageously comprises from 0.01% to 5% by weight and preferably from 0.1% to 1% by weight of alcohol.

An [alkyl polypentoside/alcohol] mass ratio of between 1 and 9 and preferably between 6 and 8 is preferred.

The surfactant has an HLB value advantageously between at least 5 and 10. The hydrophilic-lipophilic balance (HLB) value of a nonionic surfactant may be obtained by calculation according to the Griffin method (Griffin W C: "Calculation of HLB Values of Nonionic Surfactants", Journal of the Society of Cosmetic Chemists 5 (1954): 259).

The surfactant is advantageously a nonionic surfactant.

Surfactants with an HLB of less than or equal to 10 that are preferred include sorbitan esters of a non-hydroxylated aliphatic fatty acid, such as sorbitan monolaurate, sorbitan monooleate, sorbitan monostearate, sorbitan trioleate, sorbitan tristearate, sorbitan sesquioleate, and weakly ethoxylated sorbitan esters such as sorbitan stearate POE(2).

The term "aliphatic fatty acid" means a carboxylic acid, preferably a monocarboxylic acid, which is preferably aliphatic (nonaromatic), cyclic or acyclic, saturated or unsaturated and linear or branched. A saturated linear monocarboxylic acid is preferred.

According to a preferred embodiment, sorbitan monolaurate is used.

The composition advantageously comprises from 0.01% to 6% by weight and preferably from 0.1% to 2% by weight of said surfactant.

An [alkyl polypentoside/surfactant] mass ratio of between 1 and 5 and preferably between 2 and 4 is thus preferred.

According to a particularly preferred embodiment of the invention, the composition comprises sorbitan monolaurate, ethanol and an alkyl polypentoside obtained by reaction of D-xylose, 1-decanol and 1-octanol, said polypentoside having an average polymerization degree ranging from 1.4 to 1.6.

According to a preferred embodiment, the [alkyl polypentoside/ethanol] mass ratio is between 6 and 8.

According to another preferred embodiment, the [alkyl polypentoside/sorbitan monolaurate] mass ratio is between 2 and 4.

The inventors have demonstrated that a composition according to the invention can significantly improve the cutaneous penetration of active agents encapsulated in the vesicles dispersed in the composition, once it has been applied to bodily or facial skin.

Thus, the invention is particularly useful in the field of cosmetics and dermatology, for encapsulating active agents.

The cosmetic or dermatological active agent is thus at least partially encapsulated in the vesicles dispersed in the aqueous phase of the composition of the invention.

These vesicles may contain in the double layers, between the double layers and/or in the cores of the double layers an aqueous or nonaqueous phase which may contain one or more dissolved or dispersed active agents.

The composition of the invention comprises at least one cosmetic or dermatological active agent, which may be in the form of purified molecules and/or of extracts, especially plant extracts, having cosmetic or dermatological effects.

The cosmetic or dermatological agent may advantageously be chosen from compounds having antiaging activity, for preventing or retarding the appearance of the signs of aging of the skin or for slowing down or attenuating the effects thereof, or alternatively for promoting cellular or tissue longevity; active agents with skin depigmenting, bleaching or lightening activity; active agents with slimming activity; active agents with moisturizing activity; active agents with calmative, soothing, relaxing or antiinflammatory activity; active agents with stimulatory activity on cutaneous microcirculation to improve the radiance of the complexion, in particular of the face; active agents with seboregulatory activity for caring for greasy skin; active agents for cleansing or purifying the skin; active agents with free-radical-scavenging activity, and any mixture thereof.

The active agents may be chosen, for example, from:
vitamins, such as vitamin A, E or C,
antiinflammatory agents such as plant extracts, α-bisabolol, panthenol or α-tocopherol,
antiaging agents such as retinol or adenosine,
self-tanning agents such as dihydroxyacetone (DHA) or erythrulose, depigmenting agents such as kojic acid, coumaric acid or arbutin, slimming active agents such as caffeine, UV-screening agents such as benzophenone derivatives, cinnamic acid esters, salicylic acid esters, 3-benzylidenecamphor, or triazine derivatives, antioxidants such as ascorbic acid and derivatives thereof, citric acid and derivatives thereof, glutamic acid, glutamates and derivatives thereof, lactic acid and derivatives thereof, tartaric acid and derivatives thereof, bioflavonoids, butylhydroxy-hydroxyanisole, carotene and derivatives thereof, sulfites such as sodium bisulfites, and chlorobutanol, moisturizers such as glycerol, sorbitol, collagen, procollagen, gelatin, aloe vera, hyaluronic acid, urea, propanediol, butylene glycol or diglycerol.

The composition with a continuous aqueous phase of the invention may be in the form of an aqueous or aqueous-alcoholic solution, a dispersion, an aqueous or aqueous-alcoholic gel, or alternatively an oil-in-water (O/W) emulsion, intended to be applied to bodily or facial skin.

It may be in the form of creams, milks, pomades, ointments, gels or lotions, or alternatively makeup products.

The composition may also contain a gelling agent for the aqueous phase. The term "gelling agent for the aqueous phase" means a compound which increases its viscosity.

The gelling agents include, but are not limited to, polymers of natural origin such as locust bean gum, sodium alginate, agar, xanthan gum (Rhodicare XC), starches, cellulose derivatives (for example hydroxyethylcellulose, methylcellulose, carboxymethylcellulose or hydroxypropylmethylcellulose), carboxyvinyl polymers, polyvinylpyrrolidone, polyvinyl alcohol, acrylic polymers, methacrylic acid polymers, polyvinyl acetate acid polymers, vinyl chloride polymers, vinylidene chloride polymers and the like.

Optionally, mixtures of the above compounds are envisioned.

Gelling agents that are also useful are agents such as i) crosslinked acrylic acid polymers, especially copolymers of acrylic acid and of alkyl acrylate crosslinked with an allylic ether of pentaerythritol or of sucrose (acrylate/C10-C30 alkylacrylate crosspolymer), such as those sold under the brand name Pemulene (TR1 or TR2), and ii) carboxyvinyl polymers such as those sold under the brand name Carbopol.

The gelling agent is optionally present in the composition in an amount of about 0.1% to 5.0% by weight relative to the weight of the composition. In one embodiment, the gelling agent represents about 1% by weight of the cosmetic composition.

Advantageously, the composition of the invention also comprises at least one cosmetically or dermatologically acceptance excipient which may be chosen from pigments, dyes, polymers, surfactants, rheology agents, fragrances, electrolytes, pH regulators, antioxidants and preserving agents, and any mixture thereof.

Another subject of the invention is directed toward a process for preparing the composition of the invention, comprising the following steps:

the preparation of an aqueous phase advantageously comprising the cosmetic or dermatological active agent that it is desired to at least partially encapsulate in the vesicles, followed by the dispersion of the alkyl polypentoside in said aqueous phase, while providing energy especially in the form of a shear allowing the formation of vesicles at room temperature or at a higher temperature but preferably below 100° C. and preferably below 80° C., said process being characterized in that the alcohol and the surfactant having a HLB of less than 10 as described previously are each added, partially or totally, without preference either into the aqueous phase or as a mixture with the alkyl polypentoside to be dispersed in said aqueous phase.

Low-shear mixers are preferably chosen, such as pendulum stirrers equipped with one or more impellers or an anchor paddle, double-rotating stirrers equipped with a central stirrer with one or more impellers and a peripheral stirrer equipped with one or more scraping paddles matching the shape of the reactor, or alternatively kneaders and blenders. The stirring speed of these mixers is preferably greater than or equal to 500 rpm.

Another subject of the present invention is directed toward a cosmetic care method comprising the application, to the skin of at least a part of the body or the face, of a composition as described previously, especially for improving the cutaneous penetration of at least one cosmetic or dermatological active agent at least partially encapsulated in vesicles dispersed in the aqueous continuous phase of said composition.

The invention also relates to the composition described previously, for its use in the dermatological treatment of skin diseases.

According to yet another subject, the invention relates to the use of the combination i) of vesicles comprising at least one alkyl polypentoside obtained by reaction of a pentose and of at least a first and a second fatty alcohol comprising, independently of each other, a number of carbon atoms ranging from 8 to 12, each of these fatty alcohols possibly being saturated or unsaturated, and linear or branched, said polypentoside having an average polymerization degree of less than or equal to 2, and ii) of at least one surfactant having a HLB of less than 10, and iii) of at least one alcohol containing from 1 to 5 carbon atoms, for improving the cutaneous penetration of at least one cosmetic or dermatological active agent.

A subject of the invention is also the use of the combination of an alcohol containing from 1 to 5 carbon atoms and of a surfactant having a HLB of less than 10 for stabilizing vesicles formed from polypentosides comprising at least one alkyl polypentoside obtained by reaction of a pentose and of at least a first and a second fatty alcohol comprising, independently of each other, a number of carbon atoms ranging from 8 to 12, said polypentoside having an average polymerization degree of less than or equal to 2 in the aqueous phase of a composition.

The combination of the alcohol and the surfactant advantageously makes it possible to stabilize the vesicles to prevent crystallization of the polypentosides, and such that the size and shape of the vesicles remain constant over time in the cosmetic or dermatological composition.

The alcohol and the surfactant are as described previously. The alcohol is preferably a monoalcohol or a diol, advantageously ethanol.

The surfactant is preferably an ester of sorbitan and of a non-hydroxylated aliphatic fatty acid, advantageously sorbitan monolaurate.

According to a particularly preferred embodiment, use is thus made of ethanol and an ester of sorbitan and of a non-hydroxylated fatty alcohol, advantageously sorbitan monolaurate, to stabilize vesicles formed from at least one alkyl polypentoside obtained by reaction of D-xylose, and of at least two fatty alcohols comprising a number of carbon atoms ranging from 8 to 12, advantageously 1-decanol and 1-octanol, said polypentoside having an average polymerization degree of less than or equal to 2, and advantageously between 1.4 and 1.6.

The characteristics that have been described in relation to the composition are valid for describing the preparation process and the use, which are subjects of the present invention.

The invention is illustrated in greater detail in the examples that follow.

EXAMPLE 1: AQUEOUS COMPOSITION ACCORDING TO THE INVENTION

Preparation

An octyl decyl polyxylose was prepared using D-xylose and a fatty alcohol mixture in excess according to a process known to those skilled in the art, such as the process described in examples 1 and 2 of patent application EP 1750834 (AGRO INDUSTRIE RECHERCHES ET DEVELOPPEMENTS).

D-Xylose and a mixture of fatty alcohols comprising 1-decanol (first fatty alcohol, C10) and 1-octanol (second fatty alcohol, C8), in a[C10/C8] mass ratio of 90/10, were placed in contact in acidic medium.

The polyxylose obtained—noted (C8/C10) alkyl polyxylose—is used in the composition of the present example and also in comparative examples 2.1 to 2.3.

The preparation conditions were adapted so that the octyl decyl polyxylose has a degree of polymerization of about 1.5.

A composition in the form of an aqueous gel having the composition below was prepared (the percentages are given on a weight basis).

Phase A

| | |
|---|---|
| Caffeine | 1.0 |
| Phenoxyethanol | 1.0 |
| Purified water | qs 100 |

Phase B

| | |
|---|---|
| Sodium acrylates copolymer | 1.0 |
| Hydrogenated polyisobutene | 0.75 |
| Phospholipids | 0.25 |
| Polyglyceryl-10 stearate | 0.25 |
| Sunflower seed oil (*Helianthus annuus*) | 0.25 |
| Tocopheryl acetate | <0.01 |

Phase C

| | |
|---|---|
| (C8/C10) Alkyl polyxylose | 3.5 |
| Sorbitan monolaurate | 1.0 |
| Ethanol | 0.5 |

Phase A and phase B were prepared by mixing the ingredients of which they are composed. Phases A and B were mixed together to obtain a homogeneous mixture. The compounds of phase C were then added to this mixture, and a shear was applied using a stand-supported Rayneri® mixer equipped with a deflocculating paddle at a speed of 500 rpm for 15 minutes allowing the formation of multilamellar vesicles. After homogenization, the vesicles formed are dispersed in the continuous phase of the composition thus prepared.

Characterization of the Vesicles

Just after preparation of the composition, the presence of vesicles was observed by electron microscopy after freezing and cryofracture of a sample of the composition.

The method that was used is cryostripping, which makes it possible to prepare a replica of the structure observable by transmission electron microscopy. This technique comprises four essential steps:
1. freezing;
2. fracture and etching;
3. shading and formation of the replica;
4. cleaning of the replica.

Finally, visualization of the replica using a transmission electron microscope and visual analysis of the images.

The images show a homogeneous dispersion of spherical or virtually spherical objects in positive and negative and having, in the case of the multilamellar vesicles, several spherical striations at the periphery reflecting the rolling-up of several layers.

Figure 1:
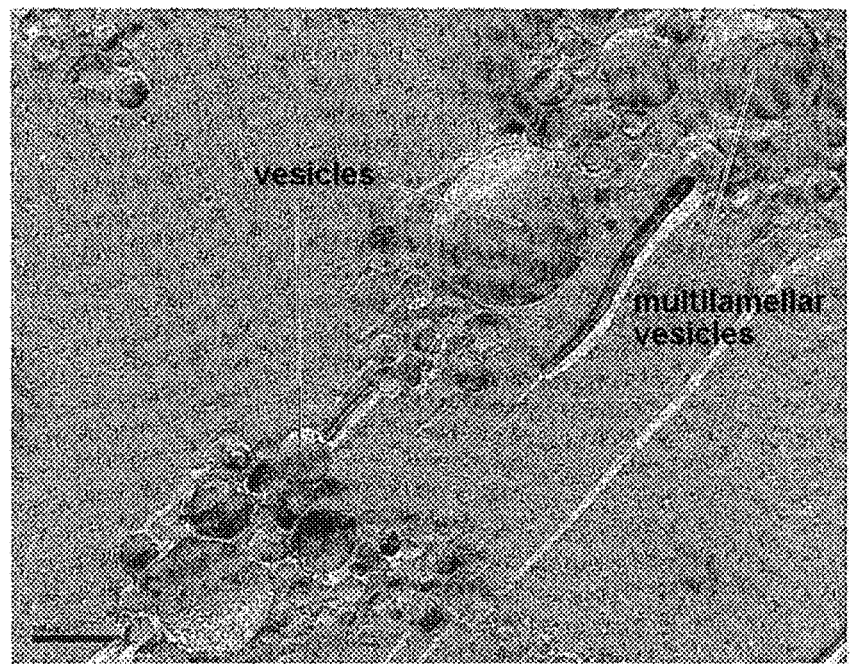
FIG. 1 is a photograph showing a dispersion of spherical objects in the medium of the composition, characteristic of the presence of multilamellar vesicles.

FIG. 1 is a photograph showing a dispersion of spherical objects in the medium of the composition, characteristic of the presence of multilamellar vesicles.

Study of Stability Over Time

Samples of each of the composition of the invention were subjected to various lighting and temperature conditions so as to test its stability.

| Stability of the composition of example 1 (table 1) | | | |
|---|---|---|---|
| | 4° C. | 45° C. | Darkness (room temperature) |
| T0 | Pale yellow gel, characteristic odor | | |
| 1 month | Stable gel | Stable gel | Stable gel |
| 1.5 months | | | Presence of vesicles in the gel (FIG. 1) |
| 15 months | Stable creamy-white gel | Yellowish color, fluid with slight release of water at the surface | Stable gel |

The composition was stored at 4° C., 25° C. and 45° C. for fifteen months and was then observed visually and on an optical microscope (magnification ×10).

Replicas of cryofractures were prepared and observed by transmission electron microscopy on samples that had not been stored and on samples that were considered stable at room temperature and in the dark after 45 days (1.5 months), according to the method described previously.

The observation under an optical microscope made it possible to confirm the presence of vesicles in the composition stored after 15 months of storage under these conditions.

Under the test conditions, the composition of the invention is as stable as the control formula free of phase C forming the vesicles (comparative example 2.4, table 2). The addition of phase C forming the vesicles in the composition does not induce any unfavorable phenomenon with regard to the stability.

In the final analysis, it is observed that the preparation of a composition that is stable over time, which comprises vesicles based on alkyl polypentoside, is possible only in the presence in the formula of an alcohol (ethanol in the present example) and of a surfactant having a HLB of less than 10 (sorbitan monolaurate in the present example).

Stability of the Control Without Vesicles

The composition having the formula below was prepared, which differs from the preceding composition in that it does not comprise the compounds of phase C, and which is thus free of vesicles (the percentages are expressed on a weight basis).

Phase A

| Caffeine | 1.0 |
| Phenoxyethanol | 1.0 |
| Water | qs 100 |

Phase B

| Sodium acrylates copolymer | 1.0 |
| Hydrogenated polyisobutene | 0.75 |
| Phospholipids | 0.25 |
| Polyglyceryl-10 stearate | 0.25 |
| Sunflower seed oil (*Helianthus annuus*) | 0.25 |
| Tocopheryl acetate | <0.01 |

Samples of the control formula were subjected to various lighting and temperature conditions so as to evaluate their stability.

Stability of the control formula without vesicles (table 2)

| | 4° C. | 45° C. | Darkness (room temperature) |
|---|---|---|---|
| T0 | | Pale yellow gel, characteristic odor | |
| 14 months | Stable white gel | Creamy-white gel, very slight release at the surface, stable | Stable pale yellow gel |

After 14 months under the conditions described in the table, the control formula does not show any significant change in its texture. The composition is stable.

EXAMPLE 2: STABILITY STUDY

Comparative Example 2.1

An aqueous composition having the formula below was prepared. The percentages are given on a weight basis.

Phase A

| Caffeine | 1.0 |
| Water | qs 100 |

Phase B

| C8/C10 alkyl polyxylose of example 1 | 15.0 |

The alkyl polyxylose prepared according to the process described in example 1 was dispersed in the caffeine solution prepared previously.

The presence of vesicles was confirmed by optical microscopy.

The composition was placed, on the one hand, in darkness at room temperature, and, on the other hand, in an oven at 4° C.

The result obtained is as follows:
After 1 month at 4° C.: appearance of crystals in the composition.
After 3 months at room temperature: appearance of crystals in the composition.

The composition prepared in this comparative example, which does not contain any alcohol or any surfactant having a HLB of less than 10 is unstable under the study conditions.

Comparative Example 2.2

An aqueous composition having the formula below was prepared, which is distinguished from that of the invention in that it does not contain any alcohol. The percentages are given on a weight basis.

Phase A

| Caffeine | 1.0 |
| Water | qs 100 |

Phase B

| C8/C10 alkyl polyxylose of example 1 | 15.0 |
| Sorbitan monolaurate | 1.0 |

The compounds of phase B were dispersed in the caffeine solution (phase A) prepared previously.

The presence of vesicles in the cosmetic composition was confirmed by optical microscopy.

The composition was stored, on the one hand, in darkness at room temperature, and, on the other hand, in an oven at 4° C.

The result obtained is as follows:
After 1 month at 4° C.: appearance of crystals in the composition.
After 3 months at room temperature: appearance of crystals in the composition.

In the absence of an alcohol, the composition prepared in this comparative example is unstable under the study conditions.

According to one variant of this comparative example, the sorbitan monolaurate was replaced with sorbitan sesquioleate (HLB=3.7).

The appearance of crystals in the composition in the course of the stability study was also observed.

Comparative Example 2.3

An aqueous composition having the formula below was prepared, which, unlike that of the invention, does not comprise any surfactant having a HLB of less than 10.

Phase A

| Caffeine | 1.0 |
|---|---|
| Water | qs 100 |
| Acrylates/C10-30 alkyl acrylate crosspolymer | 0.4 |

Phase B

| C8/C10 alkyl polyxylose of example 1 | 4.75 |
|---|---|
| Ethanol | 0.25 |

Phase A was prepared by dispersing the polymers in water.

Phase B was added, and the aqueous composition was then homogenized by gentle shear.

The presence of non-vesicular lamellar phases was observed.

In the absence of cosurfactant having a HLB of less than 10, no formed vesicle is observed in the aqueous phase, unlike what is observed for the composition of the invention.

The results are collated in the table below.

| INGREDIENTS | Example 1 | Comparative example 2.1 | Comparative example 2.2 | Comparative example 2.3 |
|---|---|---|---|---|
| Caffeine | | 1.0 | | |
| Water | | qs 100 | | |
| Acrylates/C10-30 alkyl acrylate crosspolymer | 0.4 | — | — | 0.4 |
| C8/C10 Alkyl polyxylose of example 1 | 14.75 | 15.0 | 15.0 | 14.75 |
| Sorbitan monolaurate | 1.0 | — | 1.0 | — |
| Ethanol | 0.25 | — | — | 0.25 |
| STABILITY | | | | |
| After 1 month at 4° C. | stable | crystals | crystals | no vesicles |
| After 3 months at 20° C. | stable | crystals | crystals | no vesicles |

EXAMPLE 3: STUDY OF CUTANEOUS PENETRATION

Aim of the Study

Hydrophilic active agents have difficulty in crossing the stratum corneum, the skin's more lipophilic barrier, whence the interest in vectorizing them in order to promote their penetration.

The aim of the study, performed in vitro on frozen total pig ear skin, was to evaluate the efficacy of vesicles based on alkyl polypentosides, for improving the penetration into and distribution in the surface layers of the skin of active agents that are unequally distributed, especially on account of their hydrophilicity/amphiphilicity.

Principle

The diffusion of a tracer, caffeine, across the thawed pig ear skin, mounted on a Franz diffusion cell, was measured, under occlusive conditions.

Caffeine was chosen as a tracer on account of its hydrophilicity which makes it sparingly capable of crossing the skin barrier.

A Franz diffusion cell comprises two superposed compartments communicating via the membrane used for the study.

The skin, used as membrane, is placed stratum corneum facing upwards, between these two compartments. The aqueous solution or the galenical composition to be tested containing caffeine is introduced into the upper compartment in contact with the skin. A certain amount of caffeine, dissolved in the solution or the composition, crosses the membrane constituted by the skin, and is then collected in the lower compartment in a "receiving" solution. The withdrawal apparatus collects a sample of receiving solution at regular time intervals. The samples are assayed by HPLC in order to determine the amount of caffeine that has crossed the skin. Processing of the data makes it possible to calculate the flow of caffeine, the penetration kinetics over 40 hours and also the absorption yields in 24 hours.

Implementation Conditions

Amount and mode of application:

After thawing and selection of the skins, deposition zones were determined and limited on each of these skins so that they had an area of 9 $cm^2$. Next, each composition was deposited, at a rate of 2 $mg/cm^2$, using a micropipette and applied using a finger stall presaturated with the galenicals.

The penetration kinetics were established by withdrawals of 0.2 ml of the receiving liquid at 4 hours, 8 hours, 24 hours, 28 hours, 32 hours and 46 hours, using a manual withdrawal pipette. The withdrawn samples were assayed by HPLC.

The cutaneous penetration of the active agents was, in the context of this study, mainly used for comparative purposes. Various formulations were evaluated via this technique for the purpose of demonstrating those that promote or limit the penetration of various active agents.

Formulations tested: composition of example 1 and control formulation without vesicles in accordance with comparative example 2.3.

Study parameters:

"Lara Spiral" Franz Cell:

Exposure area of 3.8 $cm^2$

Receiving volume of 6.5 ml

Receiving Solution:

10 mmol phosphate buffer 120 mmol NaCl 2.7 mmol KCl 0.1% sodium azide

Surfactant: Tween 80® at 0.5%

Quality of the Skins:

Pig ear skins that are not boiled, or tattooed, or stamped, cut into 3 cm by 3 cm pieces and extended tautly at the surface of the lower compartment of the Franz cells.

Application Conditions

Randomized deposition on each explant of 18 mg of formulation, i.e. 0.18 mg of active principle (dose corresponding to an application under the real conditions of use of a cosmetic product).

Study performed under occlusive conditions on whole skin.

Number of Replicas:

3 Franz cells for each formulation tested

Temperature and Stirring:

Mean temperature of the bath thermostatically maintained at 34° C.

Mean stirring of 200 rpm

Rainin® Withdrawal Apparatus

Rainin® manual withdrawal pipette

Figure 2:
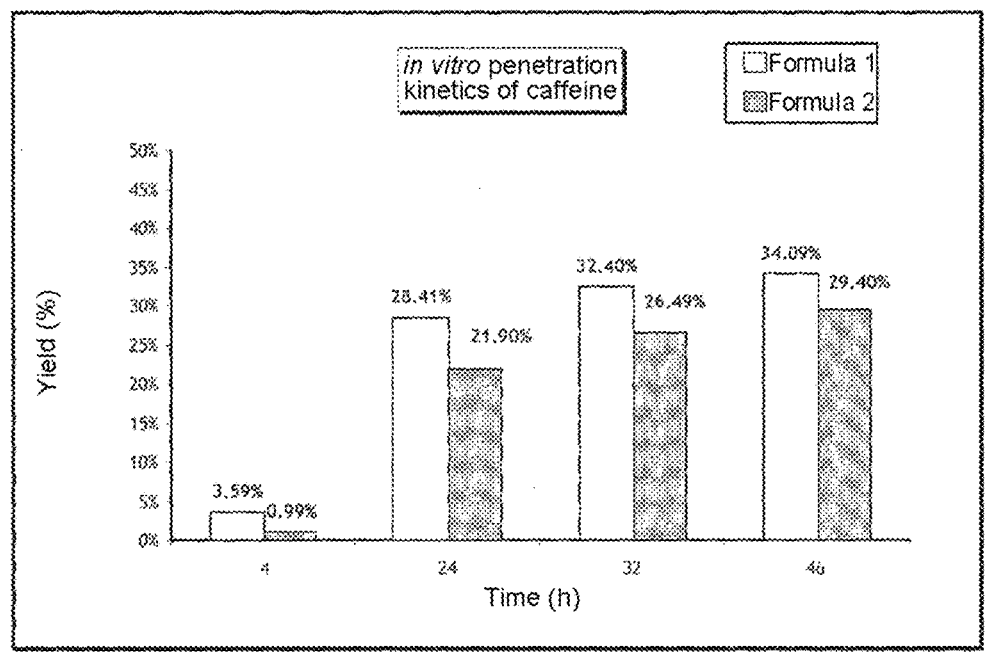
FIG. 2 shows the in vitro kinetic transmembrane diffusion results of caffeine expressed in the form of histograms bars showing in ordinates the yield expressed in percentage as a function of time in abscissae, respectively at 4 hours, 24 hours, 32 hours and 46 hours, for two formulations wherein Formulation 1 is corresponding to the composition of example1 according to the invention wherein caffeine is encapsulated in vesicles, and formulation2 is corresponding to that of the control formulation without vesicle described in comparative example 2.4. The histogram bars express the yield at different times, of the caffeine that has penetrated through the skin for the two formulations.

HPLC Assay Conditions:
Assay apparatus: Agilent®, CD 017070
Column: End capped C18 grafted RP18 HPLC column, end capped
Lichrospher® 100 RP reverse-phase apolar column (125×4) mm, 5 µm
Eluent: A=H$_2$O+0.1% HClO$_4$
B=Acetonitrile
Gradient: Isocratic 15% of B
Injection: 20 µl every 20 min
Detection: $\lambda_{caffeine}$=270 nm
Flow rate: 1 ml/min
Calibration range: dissolution of the standards from 0.5 to 500 ppm in a water/ethanol mixture (50/50).
Caffeine Concentration
In order to avoid underestimating the cutaneous absorption, the caffeine concentration in the receiving liquid needed to be less than 10% of the limit solubility concentration.
The limit solubility concentration of caffeine in the receiving liquid was 16 mg/ml.
The maximum concentration of caffeine collected during the study was less than 9.9 µg/ml.
Results The kinetic transmembrane diffusion results were expressed in the form of histograms showing this yield at 4 hours, 24 hours, 32 hours and 46 hours for the two formulations in FIG. 2. Formulation 1 corresponds to the composition of example 1 according to the invention, and formulation 2 to that of the control formulation without vesicle described in comparative example 2.3. The histogram bars express the yield at different times, of the caffeine that has penetrated through the skin for the two formulations.

At each withdrawal, larger transcutaneous passage of caffeine was observed in the case where the composition applied to the skin comprises vesicles based on alkyl polypentosides as defined previously.

The invention claimed is:

1. A cosmetic or dermatological composition comprising at least one cosmetic or dermatological active agent, at least one continuous aqueous phase, and at least one alkyl polypentoside that is obtained by reaction of a pentose with a first saturated or unsaturated, and linear or branched fatty alcohol comprising 10 carbon atoms, and a second fatty alcohol, saturated or unsaturated, and linear or branched comprising 8 carbon atoms,
wherein the composition further comprises at least one surfactant having a HLB of less than 10 and ethanol, the surfactant and ethanol being in a sufficient amount for the alkyl polypentoside to form vesicles from 0.1 to 10 µm that are dispersed in the continuous aqueous phase,
wherein the vesicles
each have a shell that is made of at least one double layer of alkyl polypentosides,
have a substantially constant average size during storage of the composition at a temperature of between 4° C. and 50° C. for a duration of at least 30 days, and
comprise said cosmetic or dermatological active agent.

2. The composition of claim 1, wherein the pentose is D-xylose.

3. The composition of claim 1, wherein the average polymerization degree of the polypentoside is between 1 and 1.8.

4. The composition of claim 1, wherein the first fatty alcohol is 1-decanol and/or the second fatty alcohol is 1-octanol.

5. The composition of claim 1, wherein the mass ratio between the first and the second fatty alcohol is between 80/20 and 99/1.

6. The composition of claim 1, wherein said composition comprises from 0.01% to 20% by weight of the alkyl polypentoside.

7. The composition of claim 1, wherein the surfactant having a HLB of less than 10 is a nonionic surfactant selected from the group consisting of sorbitan esters of a non-hydroxylated aliphatic fatty acid and weakly ethoxylated sorbitan esters.

8. The composition of claim 1, wherein the surfactant having a HLB of less than 10 is selected from the group consisting of sorbitan monolaurate, sorbitan monooleate, sorbitan monostearate, sorbitan trioleate, sorbitan tristearate, sorbitan sesquioleate and sorbitan POE(2) stearate.

9. The composition of claim 1, wherein said composition comprises sorbitan monolaurate, ethanol and an alkyl polypentoside obtained by reaction of D-xylose, 1-decanol and 1-octanol, said polypentoside having an average polymerization degree ranging from 1.4 to 1.6.

10. The composition of claim 1, wherein said composition is in the form of an aqueous solution, an aqueous-alcoholic solution, an aqueous dispersion, an aqueous gel, an aqueous-alcoholic gel, or an oil-in-water (O/W) emulsion.

11. The composition of claim 1, wherein said composition comprises at least one gelling agent for the aqueous phase selected from the group consisting of crosslinked copolymers of acrylic acid and of ethyl acrylate, and cellulose derivatives.

12. A cosmetic or dermatological composition comprising at least one cosmetic or dermatological active agent, at least one continuous aqueous phase, and at least one alkyl polypentoside that is obtained by reaction of a pentose and of at least a first and a second fatty alcohol comprising, independently of each other, a number of carbon atoms ranging from 8 to 12, each of these fatty alcohols being eventually saturated or unsaturated, and linear or branched, said polypentoside having an average polymerization degree of less than or equal to 2,
wherein the composition further comprises at least one surfactant having a HLB of less than 10 and at least one monoalcohol containing from 1 to 5 carbon atoms, the surfactant and monoalcohol being in a sufficient amount for the alkyl polypentoside to form vesicles from 0.1 to 10 µm that are dispersed in the continuous aqueous phase,
wherein the vesicles
each have a shell that is made of at least one double layer of alkyl polypentosides,
have a substantially constant average size during storage of the composition at a temperature of between 4° C. and 50° C. for a duration of at least 30 days, and
comprise said cosmetic or dermatological active agent.

13. The composition of claim 12, wherein said composition comprises from 0.01% to 5% by weight of said monoalcohol.

14. The composition of claim 12, wherein said composition comprises from 0.1% to 1% by weight of said monoalcohol.

15. The composition of claim 12, wherein said composition comprises from 0.01% to 6% by weight of said surfactant.

16. The composition of claim 12, wherein said composition comprises from 0.1% to 2% by weight of said surfactant.

17. The composition of claim 12, wherein said surfactant is sorbitan monolaurate.

18. The composition of claim 12, wherein said composition comprises an alkyl polypentoside/surfactant mass ratio ranging between 1 and 9.

19. The composition of claim 12, wherein the active agent is selected from the group consisting of compounds having antiaging activity, for preventing or retarding the appearance of the signs of aging of the skin or for slowing down or attenuating the effects thereof, or alternatively for promoting cellular or tissue longevity; active agents with skin depigmenting, bleaching or lightening activity; active agents with slimming activity; active agents with moisturizing activity; active agents with calmative, soothing, relaxing or anti-inflammatory activity; active agents with stimulatory activity on cutaneous microcirculation to improve the radiance of the complexion, in particular of the face; active agents with seboregulatory activity for caring for greasy skin; active agents for cleansing or purifying the skin; active agents with free-radical-scavenging activity, and any mixture thereof.

20. The composition of claim 12, further comprising from 0.1 to 5% by weight of at least one gelling agent for the aqueous phase.

21. A cosmetic or dermatological composition comprising at least one cosmetic or dermatological active agent, at least one continuous aqueous phase, and from 0.01% to 20% of at least one alkyl polypentoside that is obtained by reaction of D-xylose with 1-decanol, and 1-octanol, wherein the mass ratio between the 1-decanol and the 1-octanol ranges between 80/20 and 99/1;
wherein the composition further comprises from 0.01% to 6% by weight of at least one surfactant comprising sorbitan monooleate and from 0.01% to 5% by weight of ethanol, thereby having the surfactant and ethanol providing the alkyl polypentoside in the form of vesicles from 0.1 to 10 μm that are dispersed in the continuous aqueous phase,
wherein the vesicles
each have a shell that is made of at least one double layer of alkyl polypentosides,
have a substantially constant average size during storage of the composition at a temperature of between 4° C. and 50° C. for a duration of at least 30 days, and
comprise said cosmetic or dermatological active agent.

* * * * *